United States Patent
Rockley et al.

[11] Patent Number: 6,013,049
[45] Date of Patent: Jan. 11, 2000

[54] CONTROLLED OUTFLOW SLEEVE

[75] Inventors: Paul W. Rockley, Newport Coast; Kenneth E. Kadziauskas, Las Flores, both of Calif.

[73] Assignee: Allergan Sales, Inc., Irvine, Calif.

[21] Appl. No.: 09/182,383

[22] Filed: Oct. 29, 1998

[51] Int. Cl.[7] .................................................. A61B 17/20
[52] U.S. Cl. ............................... 604/22; 604/35; 604/44; 604/500; 604/119
[58] Field of Search ................................. 604/22, 27, 35, 604/43, 28, 44, 506, 521, 118, 119, 163, 164, 246, 541

[56] References Cited

U.S. PATENT DOCUMENTS

| | | |
|---|---|---|
| 3,996,935 | 12/1976 | Banko . |
| 4,203,444 | 5/1980 | Bonnell et al. . |
| 4,386,927 | 6/1983 | Eichenbaum . |
| 4,530,356 | 7/1985 | Helfgott et al. ................ 128/305 |
| 4,681,102 | 7/1987 | Bartell ................ 128/303 R |
| 4,787,889 | 11/1988 | Steppe et al. ................ 604/22 |
| 4,897,079 | 1/1990 | Zaleski et al. ................ 604/22 |
| 4,909,249 | 3/1990 | Akkas et al. ................ 606/107 |
| 4,940,468 | 7/1990 | Petillo ................ 606/170 |
| 4,983,160 | 1/1991 | Steppe et al. ................ 604/22 |
| 4,986,827 | 1/1991 | Akkas et al. ................ 606/107 |
| 5,019,035 | 5/1991 | Missirlian et al. ................ 604/22 |
| 5,026,393 | 6/1991 | Mackool ................ 623/6 |
| 5,059,204 | 10/1991 | Lawson et al. ................ 606/171 |
| 5,084,009 | 1/1992 | Mackool ................ 604/22 |
| 5,154,694 | 10/1992 | Kelman ................ 604/22 |
| 5,154,696 | 10/1992 | Shearing ................ 604/22 |
| 5,163,433 | 11/1992 | Kagawa et al. ................ 604/22 |
| 5,195,961 | 3/1993 | Takahasi et al. ................ 604/35 |
| 5,213,569 | 5/1993 | Davis ................ 604/22 |
| 5,257,988 | 11/1993 | L'Esperance ................ 606/6 |
| 5,282,786 | 2/1994 | Ureche ................ 604/22 |
| 5,286,256 | 2/1994 | Mackool ................ 604/22 |
| 5,354,265 | 10/1994 | Mackool ................ 604/22 |
| 5,505,693 | 4/1996 | Mackool ................ 604/22 |
| 5,562,612 | 10/1996 | Fox ................ 604/27 |
| 5,569,188 | 10/1996 | Mackool ................ 604/67 |
| 5,580,347 | 12/1996 | Reimeis ................ 604/30 |
| 5,634,912 | 6/1997 | Injev ................ 604/264 |
| 5,645,530 | 7/1997 | Boukhny et al. ................ 604/22 |
| 5,685,841 | 11/1997 | Mackool ................ 604/22 |
| 5,697,898 | 12/1997 | Devine ................ 604/22 |
| 5,860,949 | 1/1999 | Chen ................ 604/35 |

*Primary Examiner*—Corrine McDermott
*Assistant Examiner*—Jeremy Thissell
*Attorney, Agent, or Firm*—Walter A. Hackler

[57] ABSTRACT

Method and apparatus for removing a natural lens from an eye provides for inserting an infusion cannula into an anterior chamber of an eye and establishing fluid communication into a lens capsule from the anterior chamber. A phacoemulsification needle is inserted into the lens capsule for emulsification of a natural lens while introducing irrigation fluid into the anterior chamber and lens capsule through the infusion cannula. Emulsified lens is aspirated through a lumen in the phacoemulsification needle and a sleeve, surrounding the phacoemulsification needle, enables outflow of irrigation fluid in order to maintain intraocular pressure and cool the phacoemulsification needle.

12 Claims, 1 Drawing Sheet

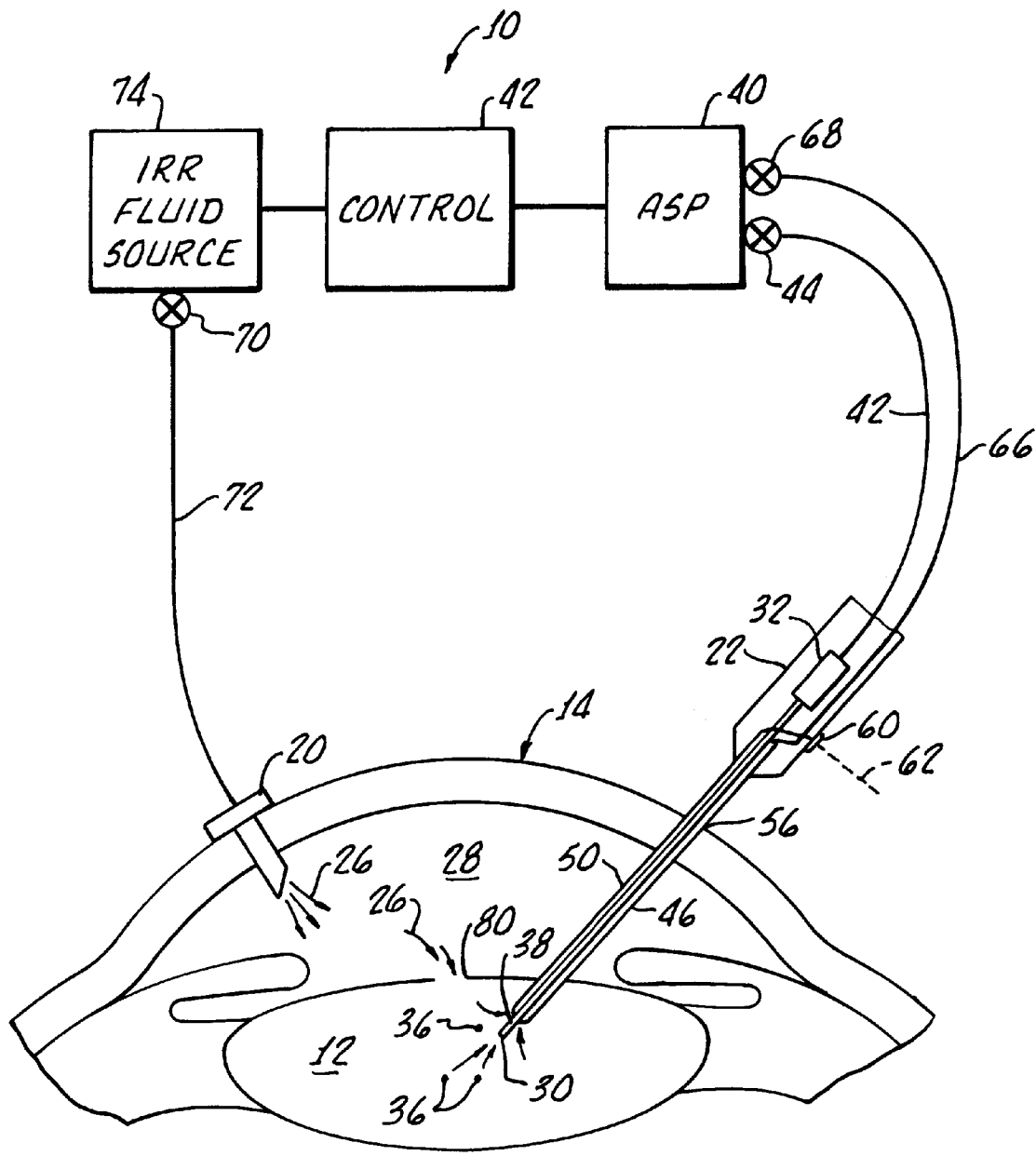

CONTROLLED OUTFLOW SLEEVE

The present invention generally relates to methods and apparatus for removing a natural lens from an eye and is more particularly directed to phacoemulsification.

A natural lens may be ultrasonically emulsified in situ through the use of a vibrating needle. This process is known as phacoemulsification. In this procedure, the emulsified lens is aspirated from the eye through a needle lumen simultaneously with the infusion of a saline solution.

Piezoelectric crystals are typically utilized to vibrate the needle and a saline solution is generally infused between an outside of the needle and a flexible shield in order to both cool the needle and maintain intraocular pressure.

An advantage of this phacoemulsification procedure is that the lens can be removed through a very small incision, for example, about 3 mm.

It is important to minimize wound leakage, that is, fluid from the eye which escapes between the sleeve and the surrounding eye tissue, and a number of attempts have been made to provide a resilient sleeve which can conform to the wound in order to minimize leakage. Unfortunately, while the elasticity of the eye tissue allows adequate manipulation of the needle within a lens capsule, a tight wound tends to compress the sleeve around the vibrating needle, thereby, allowing the heat generated by the vibrating needle to be conducted to the surrounding tissue. Such heating can cause permanent damage to epithelium tissue.

This heating problem is further compounded by the fact that emulsified lens particles aspirated through the needle lumen can occasionally plug or restrict the lumen. When this occurs, irrigation fluid introduced around the needle in between the sleeve into the eye will be stopped or restricted due to a loss of a means of fluid exit in order to prevent an unacceptable build up intraocular pressure. In some instances, fluid flow is reversed through the aspirating lumen in order to dislodge the particle. This procedure unfortunately does not provide uniform cooling of the vibrating needle and consequently, overheating of the needle may occur.

Consequently, the sleeve must be sized in order to accommodate these operating conditions and prevent undesired heating of the tissue surrounding the sleeve. If fluid could be passed through the sleeve for cooling the needle in a continuous manner, independent of needle lumen blockages, a smaller sleeve could be utilized, thus further reducing the overall cross section of the needle sleeve, which would enable yet smaller incisions to be made for the phacoemulsification procedure.

Another problem associated with the current phacoemulsification handpieces is the fact that because irrigation fluid is introduced into the eye along the needle which is also utilized for aspiration of the emulsified lens, countercurrent fluid flow occurs near the tip of the needle. That is, the irrigation fluid introduced into the eye cavity is opposite in direction to the fluid and emulsified lens aspirated through the needle. This can result in some turbulence near the needle tip which hinders the aspiration of the emulsified lens tissue.

The method and apparatus of the present invention overcome many of the problems associated with heretofore phacoemulsification handpieces.

SUMMARY OF THE INVENTION

A method in accordance with the present invention for removing a natural lens from an eye generally includes the steps of inserting an infusion cannula into an anterior chamber of the eye and establishing fluid communication into a lens capsule from the anterior chamber.

A phacoemulsification needle is inserted into the lens capsule, and an irrigation fluid is introduced into the anterior chamber and lens capsule through the infusion cannula. The natural lens is emulsified with the phacoemulsification needle and emulsified lens is aspirated through a lumen in the phacoemulsification needle.

Importantly, outflow of irrigation fluid is enabled through a sleeve surrounding the phacoemulsification needle in order to maintain both intraocular pressure and cool the phacoemulsification needle. In this manner, fluid flow through the lumen of aspirated emulsified lens and outflow of irrigation fluid around the needle are concurrent. In addition, emulsified lens particles are flushed toward the aspirating lumen, by inflow of irrigation fluid through the cannula, in order to facilitate the removal from the lens capsule.

Also, of extreme importance is the fact that the outflow of irrigation fluid is independent of lens aspiration and accordingly if restrictions or blockages in the phacoemulsification needle lumen occur, there is no concomitant change in irrigation fluid inflow or outflow which occurs with prior art phacoemulsification handpieces. Because the flow of irrigation fluid through the eye is independent of the aspiration procedure, intraocular pressure of the eye can be maintained in a more consistent manner than heretofore possible.

In addition, a constant controlled outflow of irrigation fluid around the needle provides constant cooling and accordingly the sleeve surrounding the needle can be made smaller. This occurs because the surrounding annulus of water does not need to insulate surrounding tissue from overheated needle conditions caused by a disruption of fluid flow, which occurs in prior art needle/sleeve configurations.

Apparatus, in accordance with the present invention for removing a natural lens from the eye, generally includes an irrigation cannula which provides means for introducing irrigation fluid into the eye and, in combination therewith, a phacoemulsification handpiece including needle means for phacoemulsification of a natural lens. The needle means includes a lumen for aspiration of the emulsified lens and sleeve means, surrounding the needle for, enabling outflow of irrigation fluid from the eye in order to cool the needle and maintain intraocular pressure.

More particularly, the present invention may include means for controlling an outflow rate of the irrigation fluid withdrawn from the eye, the irrigation fluid outflow rate being independent of aspiration of the emulsified lens.

Still more particularly, the means for controlling the outflow rate of irrigation fluid may include an outlet port in fluid communication with the sleeve, or, an outlet valve.

An inlet valve and fluid communication with the irrigation cannulas and control means connected to both the inlet and outlet valves may be provided for regulating flow of irrigation fluid and intraocular pressure which is independent of the aspiration of the emulsified lens through the needle lumen.

BRIEF DESCRIPTION OF THE DRAWINGS

The advantages and features of the present invention will be better understood by the following description when considered in conjunction with the accompanying drawing, in which FIG. 1 is a representation of the method and apparatus in accordance with the present invention.

DETAILED DESCRIPTION

With reference to FIG. 1, there is shown apparatus 10 for removing a natural lens, or nucleus, 12 from an eye 14, the apparatus generally including an irrigation cannula 20 and a phacoemulsification handpiece 22.

The cannula 20, which may be of any conventional design, provides a means for introducing irrigation of fluid indicated by the arrows 26 into an anterior chamber 28 of the eye 14. It should be appreciated that while the cannula 20 represents a means for introducing the irrigation fluid 26, it may also incorporate any other conventional tools or devices (not shown) which may be suitable for use in conjunction with the apparatus 10 of the present invention. Such auxiliary apparatus may include, for example, nucleus hooks, nucleus converters or other means for manipulating the nucleus being phacoemulsified.

The phacoemulsification handpiece 22 may be of any conventional type such as, for example, set forth in U.S. patent application Ser. No. 08/654,837, now U.S. Pat. No. 5,843,109, which is to be incorporated herewith in its entirety for teaching the type of phacoemulsification handpiece suitable for use in the present invention, when modified to incorporate the features of the present invention as hereinafter discussed.

In general, the handpiece 22 includes a needle which, when driven by a piezoelectric crystal device 32, provides a means for emulsification of the lens 12 and lens particles 36. The needle 30 is hollow and accordingly provides a lumen 38 which provides a means for aspiration of the emulsified lens 36. As represented in FIG. 1, the lumen 38 is interconnected to an aspiration pump 40 through an aspiration line 42. A separate valve 44 for controlling aspiration flow may be provided; however, the aspiration unit 40 typically includes a peristaltic pump (not shown) for regulating aspiration fluid which is in turn operated through a control system 42.

A sleeve 46 surrounding the needle 30 provides a means for enabling outflow of the irrigation fluid 26, introduced by the cannula 20, in order to maintain intraocular pressure and, importantly, cool the needle 30. The sleeve 46 establishes an annulus 50 surrounding the needle 30 for an outflow of irrigation fluid.

It is important to appreciate that the outflow of irrigation fluid 26 through the eye is totally independent of the operation of the needle 38 and its emulsifying lens 12 and the aspiration of lens particulates 36. Accordingly, if the lumen 38 is restricted or plugged by a lens particulate 36, no interruption or change in fluid outflow through the sleeve 46 is necessary. This results in uniform cooling of the needle 30 at all times, which enables a smaller diameter sleeve 46 to be utilized which accordingly necessitates a smaller wound, or entrance opening 56.

The sleeve 46 may be of any conventional design or preferably made in accordance with the sleeve taught in U.S. patent application Ser. No. 09/163,985, entitled: "Wound Shaper Sleeve", filed Sep. 30, 1998. This U.S. patent application is to be incorporated herewith in its entirety for teaching the type of sleeve suitable for use in combination with the handpiece 22 in the method of the present invention as hereinafter described.

The annulus 50 established by the sleeve 46 over the needle 30 may be interconnected via a port 60 connected to a discharge line 62 which provides a means for controlling an outflow rate of the irrigation fluid 26 withdrawn from the eye 14.

Alternatively, the means for controlling the outflow rate of the irrigation fluid 26 withdrawn from the eye 14 may include a line 66 interconnected to the aspiration unit 40 by a valve 68.

The means for controlling the outflow rate of the irrigation fluid may further include a valve 70 disposed between a line 72 interconnecting the cannula 20 and an irrigation fluid source 74. The control system includes circuitry (not shown) for monitoring and controlling irrigation fluid flow from the source 74 onto the aspiration unit 40 or through the exit port 60 in line 62 through the hereinabove identified valve 68, 70. The central system 42 also functions to control the aspiration of lens particulates 36 through the needle lumen 38 by way of the valve 44. It should be appreciated that any other conventional fluid control systems may be utilized in the method of the present invention.

The method of the present invention utilizing the hereinabove described apparatus includes the insertion of the infusion cannula 20 into the anterior chamber 28 of the eye 14. Fluid communication from the anterior chamber 28 to the lens capsule 12 is established by surgically providing an opening 80 in the lens capsule. The phacoemulsification needle 30 is inserted into the lens capsule 12 and irrigation fluid is introduced into the anterior chamber 28 and the lens capsule 12 through the infusion cannula 20.

The lens 12 is then emulsified with a phacoemulsification needle 30 and emulsified lens 36 is aspirated through the lumen 38 and the phacoemulsification needle 30. Irrigation fluid is then outflowed through the sleeve 46 surrounding the phacoemulsification needle 30 in order to maintain intraocular pressure and cool the phacoemulsification needle 30 as hereinabove described.

Although there has been hereinabove described a method and apparatus for removing a natural lens from an eye in accordance with the present invention, with the purpose of illustrating the manner in which the invention may be used to advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. A method for removing a natural lens from an eye, said method comprising the steps of:

inserting a n infusion cannula into an anterior chamber of the eye;

establishing fluid communication into a lens capsule from the anterior chamber;

inserting a phacoemulsification needle into the lens capsule;

introducing irrigation fluid into the anterior chamber and lens capsule through said infusion cannula;

emulsifying the natural lens with the phacoemulsification needle;

aspirating emulsified lens through a lumen in said phacoemulsification needle; and enabling outflow of irrigation fluid through a sleeve surrounding the phacoemulsification needle in order to maintain intraocular pressure and cool the phacoemulsification needle.

2. Apparatus for removing a natural lens from an eye, said apparatus comprising:

a phacoemulsification handpiece including needle means for emulsification of the natural lens, said needle means including lumen means for aspiration of emulsified lens, said phacoemulsification handpiece further including sleeve means, surrounding said needle means, for enabling outflow of irrigation fluid from the eye in order to cool said needle means and maintain intraocular pressure; and irrigation cannula means, separate from said phacoemulsification handpiece, for introducing the irrigation fluid into the eye.

3. The apparatus according to claim 2 further comprising means for controlling an outflow rate of irrigation fluid from the eye.

4. The apparatus according to claim 3 wherein the means for controlling an outflow rate of irrigation fluid comprises an outlet port in fluid communication with said sleeve means.

5. The apparatus according to claim 3 wherein the means for controlling the outflow rate of irrigation fluid comprises an outlet valve.

6. The apparatus according to claim 5 further comprising an inlet valve in fluid communication with said irrigation cannula and control means, connected to both the inlet and outlet valves, for regulating outflow of irrigation fluid independent of aspiration of emulsified lens through the needle lumen.

7. Apparatus for removing a natural lens from an eye, said apparatus comprising:

a phacoemulsification handpiece including an ultrasonically driven needle means for emulsification of the natural lens, said needle means comprising a needle with a lumen therethrough for aspiration of emulsified lens, and a single annulus around the needle for enabling outflow of irrigation fluid for cooling the needle and maintaining intraocular pressure independent of aspiration of emulsified lens through the needle lumen; and irrigation means, separate from the handpiece, for introducing the irrigation fluid into the eye.

8. The apparatus according to claim 7 wherein said separate irrigation means comprises an irrigation cannula.

9. The apparatus according to claim 8 further comprising means for controlling an outflow rate of irrigation fluid from the eye.

10. The apparatus according to claim 9 wherein the means for controlling the outflow rate of irrigation fluid comprises an outlet port in fluid communication with said sleeve means.

11. The apparatus according to claim 9 wherein the means for controlling outflow rate of irrigation fluid comprises an outlet valve.

12. The apparatus according to claim 11 further comprising an inlet valve in fluid communication with said separate irrigation cannula, and control means, connected to both the inlet and outlet valves, for regulating outflow of irrigation fluid independent of intraocular pressure and independent of aspiration of emulsified lens through the needle lumen.

* * * * *